United States Patent [19]  [11] 4,181,677
Hanifin, Jr. et al.  [45] Jan. 1, 1980

[54] 2-BENZOYL-3-ALKOXY-2-ALKENONITRILES

[75] Inventors: John W. Hanifin, Jr., Suffern; David N. Ridge, Upper Grandview, both of N.Y.

[73] Assignee: American Cyanamid Company, Stamford, Conn.

[21] Appl. No.: 968,899

[22] Filed: Dec. 13, 1978

[51] Int. Cl.² ............................................. C07C 121/75
[52] U.S. Cl. ............................ 260/465 F; 260/465 E; 424/304; 542/438; 542/440
[58] Field of Search ........................................ 260/465 F

[56] References Cited

U.S. PATENT DOCUMENTS 3,658,838   4/1972   Kiehne et al. ............... 260/465 F X
4,061,767   12/1977  Ertel et al. ....................... 260/465 D

OTHER PUBLICATIONS

Panizzi, Chemical Abstracts, vol. 42, 559–561, (1948).
Vila et al., Chemical Abstracts, vol. 47, 9940, (1952).
Edwards et al., Chemical Abstracts, vol. 50, 1505, (1956).

*Primary Examiner*—Dolph H. Torrence
*Attorney, Agent, or Firm*—Edward A. Conroy, Jr.

[57] ABSTRACT

This disclosure describes novel substituted 2-benzoyl-3-alkoxy-2-alkenonitriles and substituted 2-benzoyl-3-amino-2-alkenonitriles which are useful as intermediates for the preparation of certain substituted cis-2-benzoyl-3-hydroxy-2-alkenonitriles which possess anti-inflammatory activity.

6 Claims, No Drawings

2-BENZOYL-3-ALKOXY-2-ALKENONITRILES

BRIEF SUMMARY OF THE INVENTION

This invention relates to new organic compounds and, more particularly, is concerned with novel substituted 2-benzoyl-3-alkoxy-2-alkenonitriles (I) and novel substituted 2-benzoyl-3-amino-2-alkenonitriles (II) which may be represented by the following structural formulae:

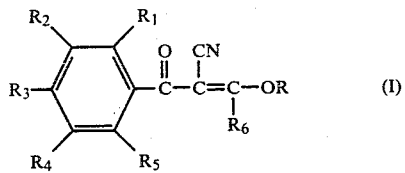

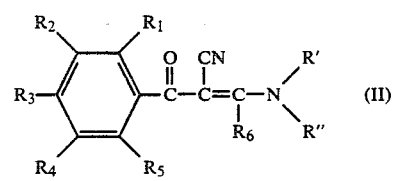

wherein $R_1$, $R_2$, $R_3$, $R_4$ and $R_5$ are each individually selected from the group consisting of hydrogen, halogen, alkyl having from 1 to 4 carbon atoms, alkoxy having from 1 to 4 carbon atoms, trifluoromethyl and trichloromethyl with the first proviso that at least two of $R_1$, $R_2$, $R_3$, $R_4$ and $R_5$ must be hydrogen in both the 3-alkoxy (I) and 3-amino (II) series with the second proviso that $R_1$, $R_2$, $R_3$, $R_4$ and $R_5$ may not all be hydrogen in the 3-alkoxy (I) series. $R_6$ is alkyl having from 1 to 4 carbon atoms, R is alkyl having from 1 to 4 carbon atoms; and R' and R" are each hydrogen or alkyl having from 1 to 4 carbon atoms and R' and R" taken together with the associated nitrogen is pyrrolidino, piperidino, morpholino, thiomorpholino or N-methylpiperazino. Halogen is exemplified by fluoro, chloro, and bromo.

DETAILED DESCRIPTION OF THE INVENTION

The novel compounds of the present invention are obtainable as crystalline materials having characteristics melting points and absorption spectra. They are appreciably soluble in many organic solvents such as lower alkanols, acetone, ethyl acetate, and the like but are generally insoluble in water.

The preparation of the novel intermediates of the present invention and their conversion to useful final products is set forth in the following reaction scheme wherein $R_1$, $R_2$, $R_3$, $R_4$, $R_5$, $R_6$, R, R' and R" are as hereinbefore defined.

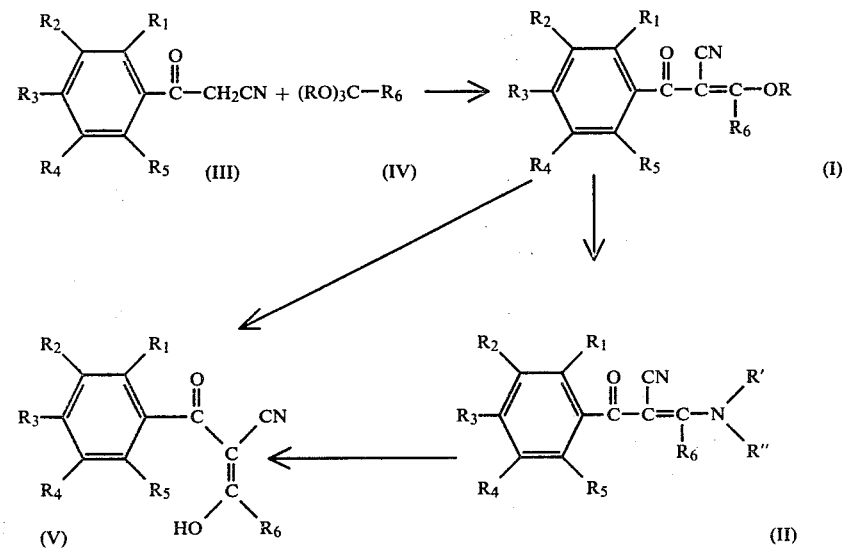

In accordance with this reaction scheme, an appropriately substituted benzoylacetonitrile (III) is condensed with a trialkyl orthoester (IV) in refluxing acetic anhydride. Evaporation of by-products and excess acetic anhydride in vacuo and purification of the residue under anhydrous conditions provides the corresponding substituted 2-benzoyl-3-alkoxy-2-alkenonitrile (I). Treatment of (I) with ammonia or a primary or secondary amine of the formula:

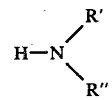

at steam bath temperature under pressure in a sealed vessel for 8–12 hours then provides the substituted 2-benzoyl-3-amino-2-alkenonitriles (II). Both of these intermediates (I) and (II) may be hydrolyzed under acidic conditions to provide the anti-inflammatory products (V). The compounds (II) wherein R' and R" are both methyl may also be prepared by treatment of an appropriately substituted benzoylacetonitrile (III) with N,N-dimethylacetamide dimethylacetal at low temperature in chloroform, methylenechloride, or even as a neat mixture of reagents.

The final products prepared from the novel intermediates of the present invention have been found to be highly useful for meliorating inflammation and inhibiting joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gm. to about 7.0 gm. of the active ingredient for a subject of about 70 kg. of body weight are administered in a 24 hour period. This dosage regimen may be adjusted to provide the optimum therapeutic response. The anti-inflammatory activity of these final products was established by the following tests.

(A) Carrageenin-induced edema in the rat

In determining the acute anti-inflammatory activity of the cis-2-benzoyl-3-hydroxy-2-alkenonitriles, Royal Hart, Wistar strain rats, ranging in weight from 80 to 90 grams were used. The rats were fasted overnight prior to dosing but had free access to water. The test compounds were administered in aqueous suspension, by gavage, in a volume of 1.7 ml. per 50 grams of rat [corresponds to hydration volume used by Winter, et al., Proc. Soc. Exp. Biol. & Med., 111, 544–547 (1962)]. The phlogistic agent used was carrageenin prepared as a sterile 1% suspension in 0.9% aqueous sodium chloride for routine testing. A volume of 0.05 ml. was injected through a 26 gauge needle into the plantar tissue of the right hind paw. Measurements were made 5 hours after drug administration (4 hours after carrageenin challenge). Volumes of both the normal and carrageenin inflamed feet were determined. The difference between the two measurements is considered to be the increased edema due to the carrageenin administration. Results are expressed as a C/T efficacy ratio (edema of control animals/edema of treated animals). Table I records the results of this test at the indicated dose level with typical final products and demonstrates the anti-inflammatory effect of these compounds in comparison with known anti-inflammatory agents.

Table I

The Effect of Anti-inflammatory Agents on Carrageenin-Induced Edema

| Compound | Number of Rats | C/T Ratio |
|---|---|---|
| Control | 8 | — |
| Aspirin | 8 | 2.86* |
| Cis-2-(m-Fluorobenzoyl)-3-hydroxycrotononitrile | 7 | 1.61* |
| Cis-3-Hydroxy-2-p-toluoylcrotononitrile | 8 | 1.41* |
| Cis-3-Hydroxy-2-p-methoxybenzoylcrotononitrile | 5 | 1.59* |
| Cis-3-Hydroxy-2-(o-anisoyl)-crotononitrile | 8 | 1.30* |
| Cis-2-(o-Fluorobenzoyl)-3-hydroxycrotononitrile | 8 | 2.18* |
| Cis-3-Hydroxy-2-($\alpha,\alpha,\alpha$-trifluoro-p-toluoyl)crotononitrile | 3 | 1.97* |

*Statistically significant activity by t test p= <.05

(B) Adjuvant-induced arthritis in the rat

The following test shows the activity of the cis-2-benzoyl-3-hydroxy-2-alkenonitriles against chronic inflammation in adjuvant induced arthritis which is accompanied by joint destruction. Groups of three Royal Hart, Wistar strain rats weighing 200±10 g. each were injected intradermally in the right hind paw with Freund's adjuvant (dried human tubercle bacilli in a mineral oil vehicle) at a dose of 2 mg./kg. of body weight. The test compounds were administered orally in a 1.5% starch vehicle at various doses once daily on days 0 to 13 post challenge. Control rats were treated in a similar manner, but given only starch vehicle. On the 14th and 21st day post challenge the diameter of the injected paw was measured by micrometer caliper. The volume of inflamed paws were estimated from these measurements and the effects of each compound are expressed as percent inhibition of swelling as compared to controls. Table II records the results of these tests conducted with representative compounds and known anti-inflammatory agents. The active compounds suppress the progression of the arthritis and associated joint deterioration.

Table II

The Effect of Anti-Inflammatory Agents on Adjuvant Induced Arthritis in Rats

| Compound | Oral Dose (mg./kg.) | Number of Rats | % Inhibition of Swelling Day 14 | % Inhibition of Swelling Day 21 |
|---|---|---|---|---|
| Normal rats | — | | — | — |
| Adjuvant Controls | — | | 0 | 0 |
| Indomethacin | 2 | 57 | 51* | 24* |
|  | 1 | 54 | 46* | 19* |
|  | 0.5 | 54 | 40* | 20* |
|  | 0.25 | 9 | 30* | 4 |
| Aspirin | 400 | 57 | 73* | 48* |
|  | 200 | 66 | 48* | 27* |
|  | 100 | 63 | 36* | 13 |
|  | 50 | 21 | 23* | 3 |
| Phenylbutazone | 150 | 27 | 75* | 44* |
|  | 75 | 39 | 62* | 28* |
|  | 37.5 | 39 | 56* | 14 |
|  | 18.8 | 21 | 31* | 7 |
| Cis-2-(p-Fluorobenzoyl)-3-hydroxycrotononitrile | 25 | 18 | 65* | 30* |
| Cis-2-(p-Chlorobenzoyl)-3-hydroxycrotononitrile | 25 | 21 | 58* | 15 |
| Cis-2-(o-Chlorobenzoyl)-3-hydroxycrotononitrile | 50 | 9 | 39* | 29 |
| Cis-2-(m-Fluorobenzoyl)-3-hydroxycrotononitrile | 50 | 9 | 48* | 37* |
| Cis-2-(3-Chloro-o-toluoyl)-3-hydroxycrotononitrile | 50 | 9 | 61* | 17 |
| Cis-3-Hydroxy-2-($\alpha,\alpha,\alpha$-trifluoro-p-toluoyl)crotononitrile | 25 | 6 | 68* | 5 |

*Statistically significant activity p= <.05 by t test

Adjuvant-induced experimental polyarthritis is a specific systemic disease of the rat which shares interesting similarities with rheumatoid arthritis. Specifically the histology of the two diseases bears a remarkable resemblance as shown by C. M. Pearson et al., Am. J. Path.

42, 73 (1963). E. M. Glenn, Am. J. Vet. Res. 27, (116), 339 (1966) has classified adjuvant-induced polyarthritis as a crippling and permanent deformity resulting from diffuse connective tissue involvement around certain susceptible joints in the rat. Zahiri et al, Can. Med. Ass. J., 101, 269 (1969) have shown that the fusiform swelling of the distal joints is associated with edema, congestion and synovitis including pannus formation, all of which precede the ultimate destruction of bone and cartilage. Furthermore, Zahiri et al., indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration [see S. Wong et al., J. Pharm. & Exp. Ther. 185, 127 (1973) and G. R. Bobalick et al., Agents and Actions 4, 364 (1974)]. The most pointed reference showing the relationship between arthritis and joint deterioration is an X-Ray analysis of adjuvant arthritis in the rat by Blackham et al., Agents and Actions 7, 145 (1977). In a similar manner, inhibition of the progress of arthritis in paws of rats treated with the compounds of this invention also lessens associated joint deterioration.

The invention will be described in greater detail in conjunction with the following specific examples.

EXAMPLE 1

3-Dimethylamino-2-(p-fluorobenzoyl)crotononitrile

To a solution of 1.6 g. of p-fluorobenzoylacetonitrile [Pihl et al., Reakts. Sposobnost Org. Soedin. Tartu. Gos. Univ., 5 (1), 27, (1968)] in 30 ml. of chloroform, cooled to −10° C., is added 1.4 g. of N,N-dimethylacetamide dimethylacetal. The reaction mixture is stirred at −10° C. for 2 hours and then evaporated in vacuo to an oil. This oil is dissolved in 150 ml. of benzene and filtered through Magnesol ®. The filtrate is evaporated to 50 ml. and petroleum ether is added to effect crystallization. The product is collected by filtration and then recrystallized from benzene-petroleum ether with charcoal treatment giving the desired product.

EXAMPLE 2

Cis-2-(p-fluorobenzoyl)-3-hydroxycrotononitrile

To a solution of 6.7 g. of p-fluorobenzoylacetonitrile in 100 ml. of chloroform, cooled to 0° C., is added 7 ml. of N,N-dimethylacetamide dimethylacetal. The reaction mixture is stirred in an ice bath for 2 hours and then at room temperature for 16 hours. The solution is evaporated in vacuo to an oil. This oil is dissolved in chloroform, filtered through Magnesol ® and then evaporated to an oil. This oil is dissolved in 100 ml. of methanol and 20 ml. of 1 N hydrochloric acid is added. The reaction mixture is heated on a steam bath for 25 minutes, cooled and the precipitate is collected. The solid is recrystallized from 50 ml. of cyclohexane, giving the desired product.

EXAMPLE 3

Cis-2-(p-chlorobenzoyl)-3-hydroxycrotononitrile

To a mixture of 68.5 g. of p-chlorobenzonitrile and 24.0 g. of sodium hydride (50% in mineral oil) in 250 ml. of ether is added, 26.1 ml. of acetonitrile and 2 ml. of isopropanol. The mixture is stirred and refluxed on a steam bath for 6 hours and then stirred overnight at room temperature. A 5 ml. portion of methanol and 250 ml. of water are added. The ether is boiled away on a steam bath and the mixture is filtered. The solid is dissolved in warm ethyl acetate and filtered. The filtrate is evaporated to a solid giving β-amino-4-chlorocinnamonitrile.

A 94.68 g. portion of β-amino-4-chlorocinnamonitrile is suspended in 250 ml. of water. A 50 ml. portion of concentrated hydrochloric acid is added and the mixture is stirred overnight. The solid is collected and stirred for 4 hours in a mixture of 250 ml. of water, 250 ml. of ethanol and 50 ml. of concentrated hydrochloric acid. The reaction mixture is evaporated and the solid is taken up in methylene chloride and passed through Magnesol ®. The filtrate is evaporated on a steam bath with the addition of hexanes giving crystals of p-chlorobenzoylacetonitrile.

A 9.0 g. portion of p-chlorobenzoylacetonitrile in 100 ml. of chloroform is reacted with 10 ml. of N,N-dimethylacetamide dimethylacetal and treated as described in Example 2, giving the desired product.

EXAMPLE 4

Cis-2-(o-chlorobenzoyl)-3-hydroxycrotononitrile

A 150 ml. portion of ammonia is condensed in a reaction flask and a small piece of sodium is added. The blue color is discharged by the addition of ferric chloride and 3.22 g. of sodium are added. After the color is discharged, 5.75 ml. of acetonitrile in 10 ml. of diethyl ether are added. The reaction is cooled in a dry ice-acetone bath and 13.3 g. of 2-chlorobenzonitrile in 25 ml. of tetrahydrofuran are added dropwise. The ammonia is allowed to evaporate, the solvent is blown off with nitrogen and water is added. The mixture is extracted with methylene chloride. The organic extracts are dried over sodium sulfate and filtered through Magnesol ®. The filtrate is evaporated with the addition of hexanes giving β-amino-2-chlorocinnamonitrile as a white crystalline solid.

A 45 ml. portion of 1 N hydrochloric acid is added to the β-amino-2-chlorocinnamonitrile and the reaction is stirred overnight. The solid is collected, washed with water, dried, taken up in methylene chloride and passed through Magnesol ®. The filtrate is evaporated on a steam bath with the addition of hexanes giving o-chlorobenzoylacetonitrile as a white crystalline solid.

The 4.4 g. portion of o-chlorobenzoylacetonitrile in 50 ml. of chloroform is reacted with 5 ml. of N,N-dimethylacetamide dimethylacetal as described in Example 2, giving the desired product.

EXAMPLE 5

Cis-2-(m-fluorobenzoyl)-3-hydroxycrotononitrile

To a solution of 4.7 g. of m-fluorobenzoylacetonitrile [Pihl, et al., Reakts. Sposabnost. Org. Soedin, Tartu. Gos. Univ., 5 (1), 27 (1968)] in 50 ml. of chloroform, cooled in an ice bath, is added 5 ml. of N,N-dimethylacetamide dimethylacetal. The reaction mixture is stirred at 0° C. for 2 hours then at room temperature for 16 hours. The solution is evaporated in vacuo to an oil. The oil is dissolved in 50 ml. of methanol and 15 ml. of 1 N hydrochloric acid is added. The reaction mixture is heated on a steam bath for 30 minutes and then evaporated in vacuo to an oil. This oil is added to 75 ml. of benzene and extracted three times with a saturated solution of sodium bicarbonate. The combined aqueous phase is washed with benzene, acidified with concentrated hydrochloric acid and the precipitate is collected and recrystallized from isopropanol with charcoal treatment giving the desired product.

EXAMPLE 6

Cis-2-(o-fluorobenzoyl)-3-hydroxycrotononitrile

A 9.8 g. portion of o-fluorobenzoylacetonitrile [Dorsch et al., J. A. C. S. 54, 2960 (1932)] in 100 ml. of chloroform is cooled in an ice-water bath. A 10 ml. portion of N,N-dimethylacetamide dimethylacetal is added and the mixture is stirred in an ice bath for 2 hours and then at room temperature overnight. The mixture is evaporated to an oil, dissolved in 50 ml. of methanol, acidified with 20 ml. of 1 N hydrochloric acid, heated on a steam bath for ½ hour and evaporated to an oil. A 100 ml. portion of chloroform and 100 ml. of saturated aqueous sodium bicarbonate solution are added. The mixture is shaken and the organic phase is again extracted with saturated aqueous sodium bicarbonate solution. The aqueous phases are washed with chloroform, acidified with concentrated hydrochloric acid and the solid is collected, washed with water and recrystallized from hot isopropanol with charcoal treatment giving the desired product.

EXAMPLE 7

Cis-2-(3-chloro-o-toluoyl)-3-hydroxycrotononitrile

A 45.0 g. portion of potassium tertiary butoxide is added to 700 ml. of diethyl ether and then cooled in an ice-salt bath. To this is added, over 15 minutes, a mixture of 60.0 g. of 3-chloro-2-methylbenzonitrile and 22.0 ml. of acetonitrile in 300 ml. of diethyl ether. The mixture is stirred in the ice bath for ½ hour, allowed to warm to room temperature and then stirred for one hour. This mixture is poured into one liter of water and the layers are spearated. The aqueous phase is extracted with diethyl ether and the ether layers are combined, washed four times with water and dried over magnesium sulfate. The crystals which form on evaporation are collected and recrystallized from 200 ml. of hot benzene giving 16.0 g. of β-amino-3-chloro-2-methylcinnamonitrile.

An 11.0 g. portion of the above product is added to 150 ml. of methanol and heated to solution on a steam bath. A 50 ml. portion of 1 N hydrochloric acid is added and the mixture is heated on the steam bath for 3 hours. The mixture is cooled, 30 ml. of water are added, the precipitate is collected and air dried. This solid is recrystallized from 80 ml. of hot methanol with charcoal treatment giving 7.8 g. of 3-chloro-2-methylbenzoylacetonitrile.

A 5.4 g. portion of the above ketone in 75 ml. of chloroform is reacted with 60 ml. of N,N-dimethylacetamide dimethylacetal and treated as described in Example 2, to give the desired product.

EXAMPLE 8

Cis-3-hydroxy-2-(p-toluoyl)crotonitrile

To a solution of 10 g. of α-bromo-p-methyl acetophenone in 50 ml. of ethanol in an ice bath is added dropwise a solution of 6.4 g. of sodium cyanide in 30 ml. of water, at a rate so that the temperature is maintained at 25°-30° C. The mixture is then stirred at room temperature for 2 hours, drowned in 600 ml. of water and filtered through Celite ®. The filtrate is acidified to pH 5 with acetic acid, allowed to stand 10 minutes and then filtered. The solid is dissolved in 100 ml. of boiling benzene, magnesium sulfate is added together with charcoal and the mixture is filtered. A 400 ml. portion of hexane is added to the filtrate and the mixture is cooled giving 3.0 g. of p-methylbenzoylacetonitrile.

A 2.6 g. portion of p-methylbenzoylacetonitrile in 30 ml. of chloroform is cooled in an ice bath. A 3 ml. portion of N,N-dimethylacetamide dimethylacetal is added and the mixture is allowed to stand in an ice bath for 2 hours and then at room temperature for 48 hours. The mixture is evaporated to an oil which is dissolved in 20 ml. of methanol. A 3 ml. portion of 1 N hydrochloric acid is added and the mixture is heated on a steam bath for ½ hour and evaporated to a dark oil. This oil is dissolved in 75 ml. of benzene and extracted with three 50 ml. portions of saturated aqueous sodium bicarbonate. The combined aqueous phases are washed with benzene and acidified with concentrated hydrochloric acid. The precipitate is collected and recrystallized from 20 ml. of hot isopropanol with charcoal treatment, giving the desired product.

EXAMPLE 9

Cis-3-hydroxy-2-(o-anisoyl)crotononitrile

A 10.0 g. portion of α-bromo-o-methoxyacetophenone is suspended in 50 ml. of ethanol. A solution of 6.4 g. of sodium cyanide in 30 ml. of water is added as described in Example 8. Following the procedure of Example 8, there is obtained o-methoxybenzoylacetonitrile.

A 3.1 g. portion of o-methoxybenzoylacetonitrile is added to 50 ml. of chloroform cooled in an ice bath. A 3.5 ml. portion of dimethylacetamide dimethylacetal is added and the mixture is stirred in an ice bath for 2 hours and then at room temperature overnight. The mixture is evaporated to an oil which is dissolved in 25 ml. of methanol. A 5 ml. portion of 1 N hydrochloric acid is added and the mixture is heated on a steam bath for ½ hour and then evaporated to an oil. This oil is dissolved in 50 ml. of benzene. A 50 ml. portion of saturated aqueous sodium bicarbonate solution is added forming two layers. The benzene layer is extracted with two 50 ml. portions of saturated aqueous sodium bicarbonate solution. The aqueous phases are combined, washed twice with 50 ml. of benzene and acidified with concentrated hydrochloric acid. The solid is collected, washed with water and recrystallized from hot isopropanol, with charcoal treatment, giving the desired product.

EXAMPLE 10

Cis-3-hydroxy-2-(p-methoxybenzoyl)crotononitrile

A 25.0 g. portion of α-bromo-p-methoxyacetophenone is suspended in 125 ml. of ethanol. A solution of 16.0 g. of sodium cyanide in 75 ml. of water is added, using an ice-water bath to keep the temperature at 25°-30° C. The mixture is stirred for 45 minutes at room temperature. A total of 1.2 liters of water is added in 200 ml. increments with filtration through celite until no more precipitate forms. The filtrate is acidified to pH 5 with acetic acid. The solid is collected, washed with water, dried and recrystallized from benzene giving p-methoxybenzoylacetonitrile.

A 4.7 g. portion of p-methoxybenzoylacetonitrile is added to 50 ml. of chloroform, cooled in an ice bath. A 5 ml. portion of N,N-dimethylacetamide dimethylacetal is added and the mixture is stirred in an ice bath for 2 hours and then at room temperature overnight. The mixture is evaporated to an oil which is dissolved in 25 ml. of methanol. A 5 ml. portion of 1 N hydrochloric acid is added, the mixture is heated on a steam bath for ½ hour and then evaporated to an oil. A 70 ml. portion of saturated aqueous sodium bicarbonate solution and 70 ml. of benzene are added and the mixture separates into two layers. The benzene layer is extracted twice with saturated aqueous sodium bicarbonate solution. The aqueous phases are combined, washed twice with benzene, acidified with 12 N hydrochloric acid and the solid is collected. This solid is recrystallized from 50 ml. of hot isopropanol with charcoal treatment giving the desired product.

EXAMPLE 11

Cis-2-(3,4-difluorobenzoyl)-3-hydroxycrotononitrile

A solution of 10.2 g. of 3,4-difluorobenzoylacetonitrile, 9.2 g. of triethyl orthoacetate and 20 ml. of acetic anhydride is heated on a steam bath for 0.5 hour and then poured into 200 ml. of water which is then heated on the steam bath for 2 hours. On cooling, the solid is filtered and then dissolved in methylene chloride. This solution is extracted with two portions of aqueous sodium bicarbonate and the aqueous extracts are combined and acidified with concentrated hydrochloric acid. The precipitate is extracted into methylene chloride, passed through a pad of Magnesol ®, heated and diluted with hexane. Upon cooling, colorless crystals result, yielding the title compound, m.p. 51°–54° C.

Similarly prepared are cis-2-(2,5-difluorobenzoyl)-3-hydroxycrotononitrile, cis-2-(3,4,5-trimethoxybenzoyl)-3-hydroxycrotononitrile, cis-2-(2,4,6-trimethylbenzoyl)-3-hydroxycrotononitrile, and cis-2-(2,5-dichlorobenzoyl)-3-hydroxycrotononitrile.

EXAMPLE 12

2-(p-Fluorobenzoyl)-3-methoxycrotononitrile

A solution containing 55.8 g. (0.34 mole) of p-fluorobenzoylacetonitrile, 41 g. (0.34 mole) of trimethyl orthoacetate, and 90 g. (0.88 mole) of acetic anhydride is heated to reflux for 5 hours. The excess solvent and volatile by-products are then removed by vacuum distillation and the residue is recrystallized from diethyl ether. Alternatively, the distillation residue may be distilled over on a Kugelrohr apparatus at 160° C./0.25 mm. to provide a viscous oil which may be crystallized from diethyl ether to provide the pure title compound.

EXAMPLE 13

2-(p-Fluorobenzoyl)-3-ethoxycrotononitrile

A solution of 16.3 g. of p-fluorobenzoylacetonitrile and 18.3 ml. of triethyl orthoacetate in 35 ml. of acetic anhydride is heated on a steam bath for 2.5 hours. The solvents are removed in vacuo and the residue is distilled at 165°–167° C./300μ. Upon cooling, this distillate solidifies and is recrystallized from methylene chloride/hexane to give the desired 2-(p-fluorobenzoyl)-3-ethoxycrotononitrile, m.p. 77°/89° C.

EXAMPLE 14

Cis-2-(p-fluorobenzoyl)-3-hydroxycrotononitrile

A solution of 5 g. of 2-(p-fluorobenzoyl)-3-methoxycrotononitrile in 50 ml. of ethanol is treated with 25 ml. of 3 N aqueous hydrochloric acid at room temperature for one hour. The solvent is evaporated, the residue diluted with water, and the product is extracted with chloroform. The organic phase is separated, dried, filtered and evaporated to provide the title compound.

EXAMPLE 15

2-Benzoyl-3-methylaminocrotononitrile

In the glass liner of a stainless steel bomb cooled to −78° is condensed 10 ml. of methylamine. To this is added 0.5 ml. of 2 M n-butyllithium (in hexane), followed by 5.0 g. of 2-benzoyl-3-methoxycrotononitrile. The bomb is sealed and heated on a steam bath overnight. The bomb is then cooled, opened and the contents evaporated. The residue is dissolved in chloroform, passed through a Magnesol ® pad and the filtrate is evaporated. The residue is recrystallized from chloroform-hexane yielding the title compound.

EXAMPLE 16

2-Benzoyl-3-butylaminocrotononitrile

A sample of 2.5 g. of 2-benzoyl-3-methoxycrotononitrile is dissolved in 10 ml. of n-butylamine. The solution is sealed in a stainless steel bomb and heated on a steam bath overnight. The bomb is then opened and the solvent evaporated under reduced pressure. A greenish oil is obtained which is distilled on a Kugelrohr apparatus at 200° C./0.1 mm. to obtain the yellow oily product.

EXAMPLE 17

2-Benzoyl-3-dimethylaminocrotononitrile

To a solution of 14.5 g. (0.10 m) of benzoylacetonitrile in 100 ml. of chloroform, cooled in an ice-salt bath, was added 13.3 g. (0.1 m) of N,N-dimethylacetamide dimethylacetal in 20 ml. chloroform. The reaction mixture was stirred in the ice-salt bath for 2 hours, then evaporated in vacuo to an orange oil. The oil was dissolved in 150 ml. benzene and passed through Magnesol ®. The filtrate was evaporated and the oil thus obtained was dissolved in 50 ml. benzene to which pet ether was added until the solution became cloudy. The precipitate which formed upon cooling was collected. The solid was recrystallized twice from benzene-pet ether, with charcoal treatment to yield 5.8 g. (27%) of light yellow crystals, m.p. 105°–106° C.

EXAMPLE 18

Cis-2-benzoyl-3-hydroxycrotononitrile

A solution of 1.35 g. (0.006 m) of 2-benzoyl-3-dimethylaminocrotononitrile in a mixture of 15 ml. methanol and 8 ml. of 1 N HCl was heated on the steam bath in an open beaker for 45 minutes. Upon cooling in an ice bath, a solid formed, was collected and then recrystallized from cyclohexane-pet ether with charcoal treatment, giving 0.7 g. (64%) light pinkish crystals, m.p. 71°–73° C.

EXAMPLE 19

2-Benzoyl-3-methoxy-2-pentenonitrile

A solution containing 30 g. of benzoylacetonitrile, 36.4 g. of triethylorthopropionate and 57 g. of acetic anhydride is heated in an oil bath at 130° for 3 hours. The ethanol and excess acetic anhydride is distilled off and the residue is diluted with chloroform. The chloroform solution is passed quickly through Magnesol ® and concentrated, then cooled to produce the title product. Similarly prepared is 2-benzoyl-3-methoxy-2-hexenonitrile and 2-benzoyl-3-methoxy-2-heptenonitrile.

EXAMPLE 20

Cis-2-benzoyl-3-hydroxy-2-pentenonitrile

A two-phase mixture of 5.0 g. 2-benzoyl-3-methoxy-2-pentenonitrile in 50 ml. of chloroform is stirred with a 50 ml. solution of aqueous 1 N hydrochloric acid. After 24 hours, the organic phase is separated and evaporated. The residue is recrystallized from chloroform to yield the title compound. Similarly, cis-2-benzoyl-3-hydroxy-2-hexenonitrile is prepared from 2-benzoyl-3-methoxy-2-hexenonitrile and cis-2-benzoyl-3-hydroxy-2-heptenonitrile is prepared from 2-benzoyl-3-methoxy-2-heptenonitrile.

EXAMPLE 21

2-Benzoyl-3-N-piperidylcrotononitrile

To a solution of 5.0 g. of 2-benzoyl-3-methoxycrotononitrile in 50 ml. of dry tetrahydrofuran is added 5 ml. of piperidine. The reaction is heated to reflux for 2 hours, cooled and evaporated in vacuo. The residue is recrystallized from chloroform/hexane to provide the crystalline title compound.

Similarly prepared are 2-benzoyl-3-N-piperidylcrotononitrile, 2-benzoyl-3-N-pyrazoylcrotononitrile and 2-benzoyl-3-N-piperazlcrotononitrile.

EXAMPLE 22

2-Benzoyl-3-dimethylaminocrotononitrile

A volume of 10 ml. of diethylamine is condensed in a glass tube at −78° C. A sample of 5 g. of 2-benzoyl-5-methoxycrotononitrile is added, the tube is sealed in a stainless steel bomb and heated on a steam bath overnight. The bomb is then cooled, opened, and the contents evaporated. The residue was recrystallized from chloroform to provide the title compound.

Similarly prepared were 2-benzoyl-3-diethylaminocrotononitrile and 2-benzoyl-3-di-isopropylaminocrotononitrile.

EXAMPLE 23

2-(p-Fluorobenzoyl)-3-dimethylaminocrotononitrile

Dimethylamine is bubbled into a solution of 2-(p-fluorobenzoyl)-3-ethoxycrotononitrile in 50 ml. of diethyl ether for 15 minutes. After stirring at room temperature for one hour, the reaction mixture is allowed to evaporate to dryness and the resulting solid is recrystallized from methylene chloride/hexane to give 2-(p-fluorobenzoyl)-3-dimethylaminocrotononitrile, m.p. 65°–67° C.

EXAMPLE 24

2-(p-Fluorobenzoyl)-3-methylaminocrotononitrile

The procedure of Example 15 is repeated substituting an equimolecular amount of 2-(p-fluorobenzoyl)-3-methoxycrotononitrile for the 2-benzoyl-3-methoxycrotononitrile employed in that example. There is thus obtained the title compound after purification by column chromatography.

EXAMPLE 25

2-(p-Fluorobenzoyl)-3-butylaminocrotononitrile

By replacing the 2-benzoyl-3-methoxycrotononitrile employed in Example 16 with an equimolar amount of 2-(p-fluorobenzoyl)-3-methoxycrotononitrile, there is obtained the title compound in equally good yield.

EXAMPLE 26

2-(p-Fluorobenzoyl)-3-dimethylaminocrotononitrile

The general procedure of Example 17 is repeated but replacing the benzoylacetonitrile employed in that example with an equivalent amount of p-fluorobenzoylacetonitrile whereby there is obtained the title compound after recrystallization from benzene/petroleum ether.

EXAMPLE 27

Cis-2-(5-chloro-o-toluoyl)-3-hydroxycrotononitrile

A 45.0 g. portion of potassium tertiary butoxide is added to 700 ml. of diethyl ether and then cooled in an ice-salt bath. To this is added, over 15 minutes, a mixture of 60.0 g. of 5-chloro-2-methylbenzonitrile and 22.0 ml. of acetonitrile in 300 ml. of diethyl ether. The mixture is stirred in the ice bath for ½ hour, allowed to warm to room temperature and then stirred for one hour. This mixture is poured into one liter of water and the layers are separated. The aqueous phase is extracted with diethyl ether and the ether layers are combined, washed four times with water and dried over magnesium sulfate. The crystals which form on evaporation are collected and recrystallized from 200 ml. of hot benzene giving 16.0 g. of β-amino-5-chloro-2-methylcinnamonitrile.

An 11.0 g. portion of the above product is added to 150 ml. of methanol and heated to solution on a steam bath. A 50 ml. portion of 1 N hydrochloric acid is added and the mixture is heated on the steam bath for 3 hours. The mixture is cooled, 30 ml. of water are added, the precipitate is collected and air dried. This solid is recrystallized from 80 ml. of hot methanol with charcoal treatment giving 7.8 g. of 5-chloro-2-methylbenzoylacetonitrile.

A 5.4 g. portion of the above ketone in 75 ml. of chloroform is reacted with 60 ml. of N,N-dimethylacetamide dimethylacetal and treated as described in Example 2, to give the desired product.

EXAMPLE 28

Cis-2-(2,4-dichlorobenzoyl)-3-hydroxycrotononitrile

A 150 ml. portion of ammonia is condensed in a reaction flask and a small piece of sodium is added. The blue color is discharged by the addition of ferric chloride and 3.22 g. of sodium are added. After the color is discharged, 5.75 ml. of acetonitrile in 10 ml. of diethyl ether are added. The reaction is cooled in a dry ice-acetone bath and 16.6 g. of 2,4-dichlorobenzonitrile in 25 ml. of tetrahydrofuran are added dropwise. The ammonia is allowed to evaporate, the solvent is blown off with nitrogen and water is added. The mixture is extracted with methylene chloride. The organic extracts are dried over sodium sulfate and filtered through Magnesol ®. The filtrate is evaporated with the addition of hexanes giving β-amino-2,4-dichlorocinnamonitrile as a white crystalline solid.

A 45 ml. portion of 1 N hydrochloric acid is added to the β-amino-2,4-dichlorocinnamonitrile and the reaction is stirred overnight. The solid is collected, washed with water, dried, taken up in methylene chloride and passed through Magnesol ®. The filtrate is evaporated on a steam bath with the addition of hexanes giving 2,4-dichlorobenzoylacetonitrile as a white crystalline solid.

A 4.4 g. portion of 2,4-dichlorobenzoylacetonitrile in 50 ml. of chloroform is reacted with 5 ml. of N,N-dimethylacetamide dimethylacetal as described in Example 2, giving the desired product.

We claim:

1. A compound of the formula:

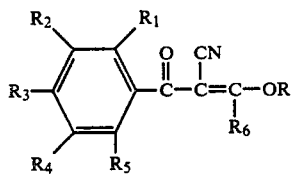

wherein $R_1$, $R_2$, $R_3$, $R_4$ and $R_5$ are each individually selected from the group consisting of hydrogen, halogen, alkyl having up to 4 carbon atoms, alkoxy having up to 4 carbon atoms, trifluoromethyl and trichloromethyl with the proviso that at least two of $R_1$, $R_2$, $R_3$, $R_4$ and $R_5$ must be hydrogen but $R_1$, $R_2$, $R_3$, $R_4$ and $R_5$ may not all be hydrogen; $R_6$ is alkyl having up to 4 carbon atoms; and R is alkyl having up to 4 carbon atoms.

2. The compound according to claim 1 wherein $R_1$ and $R_5$ are both hydrogen, $R_2$, $R_3$ and $R_4$ are all methoxy, and R and $R_6$ are both methyl; 2-(3,4,5-trimethoxybenzoyl)-3-methoxy-2-pentenonitrile.

3. The compound according to claim 1 wherein $R_1$, $R_2$, $R_4$ and $R_5$ are hydrogen, $R_3$ is fluoro, and R and $R_6$ are both methyl; 2-(p-fluorobenzoyl)-3-methoxy-crotononitrile.

4. The compound according to claim 1 wherein $R_1$, $R_2$, $R_4$ and $R_5$ are hydrogen, $R_3$ is trifluoromethyl, R is ethyl and $R_6$ is methyl; 3-ethoxy-2-(p-trifluoromethylbenzoyl)crotononitrile.

5. The compound according to claim 1 wherein $R_2$ is fluoro, $R_1$, $R_3$, $R_4$ and $R_5$ are hydrogen, $R_6$ is ethyl and R is methyl; 2-(m-fluorobenzoyl)-3-methoxy-2-pentenonitrile.

6. The compound according to claim 1 wherein $R_1$ is chloro, $R_2$, $R_3$, $R_4$ and $R_5$ are hydrogen, R is ethyl and $R_6$ is ethyl; 2-(o-chlorobenzoyl)-3-ethoxy-2-pentenonitrile.

* * * * *